United States Patent
Kamen et al.

[11] Patent Number: 6,155,824
[45] Date of Patent: Dec. 5, 2000

[54] APPARATUS AND METHOD FOR CLEANING TEETH

[75] Inventors: Dean L. Kamen, Bedford; Larry B. Gray, Merrimack, both of N.H.

[73] Assignee: Deka Products Limited Partners, Manchester, N.H.

[21] Appl. No.: 09/280,144

[22] Filed: Mar. 26, 1999

Related U.S. Application Data

[60] Provisional application No. 60/079,502, Mar. 26, 1998.

[51] Int. Cl.$^7$ ................................................. A61C 17/02
[52] U.S. Cl. .............................. 433/80; 433/88; 601/162; 604/35
[58] Field of Search .................... 433/80, 88, 89, 433/116; 604/27, 35; 601/162–165; 451/75, 90

[56] References Cited

U.S. PATENT DOCUMENTS

| | | | |
|---|---|---|---|
| 3,065,749 | 11/1962 | Brass | 433/88 |
| 3,211,149 | 10/1965 | Fono | 601/164 |
| 3,452,746 | 7/1969 | Shawhouse | 601/163 |
| 4,020,596 | 5/1977 | Bergh . | |
| 4,111,193 | 9/1978 | Jousson | 601/162 |
| 4,540,365 | 9/1985 | Nelson et al. | 433/88 |
| 4,692,140 | 9/1987 | Olson | 604/35 |
| 4,776,794 | 10/1988 | Meller | 433/216 |
| 4,801,292 | 1/1989 | Watson | 604/36 |
| 4,903,688 | 2/1990 | Bibby et al. | 128/66 |
| 4,941,459 | 7/1990 | Mathur | 128/66 |
| 5,088,515 | 2/1992 | Kamen | 137/15 |
| 5,145,367 | 9/1992 | Kasten | 433/80 |
| 5,286,192 | 2/1994 | Dixon | 433/80 |
| 5,321,865 | 6/1994 | Kaeser | 601/162 |
| 5,460,604 | 10/1995 | Arnett et al. | 604/35 |
| 5,542,918 | 8/1996 | Atkinson | 604/35 |
| 5,547,376 | 8/1996 | Harrel | 433/116 |
| 5,564,629 | 10/1996 | Weissman et al. | 239/8 |
| 5,634,791 | 6/1997 | Matsuura et al. | 433/88 |

FOREIGN PATENT DOCUMENTS

| | | |
|---|---|---|
| 2 455 456 | 11/1980 | France . |
| 2 588 469 | 4/1987 | France . |

OTHER PUBLICATIONS

Equipment Profile for Micadent II, Medidente International, Inc., http://www.medidenta.com/equip/micadent/index.html, Oct. 15, 1999.

*Primary Examiner*—Ralph A. Lewis
*Attorney, Agent, or Firm*—Bromberg & Sunstein LLP

[57] ABSTRACT

An apparatus designed to clean surfaces and to recycle the cleaning solution including a hand-holdable housing, a tube having a lumen through which cleaning solution may be impelled, a pump for both impelling and urging solution back through a return path. Piston-based, in particular a ganged pump using a stepped piston, as well as membrane-based pumps are disclosed. Methods of cleaning surfaces using such apparatuses as well as a system for periodically cleaning a plurality of surfaces are disclosed as additional embodiments.

26 Claims, 13 Drawing Sheets

APPARATUS AND METHOD FOR CLEANING TEETH

RELATED U.S. APPLICATION

The present application claims priority from Provisional Application Serial No. 60/079,502, filed Mar. 26, 1998, which is hereby incorporated herein by reference.

TECHNICAL FIELD

The present invention relates to apparatuses for and methods of cleaning teeth and other surfaces within the oral cavities of users.

BACKGROUND ART

It is well known that solutions containing baking soda or other abrasive materials serve as excellent media for cleaning teeth. There are many known devices which provide delivery of such solutions thereby offering effective oral hygiene to the user. These devices are typically large complicated systems intended for professional use in a dentist's office.

SUMMARY OF THE INVENTION

The invention provides an apparatus designed to pump an appropriate amount of cleaning solution into an oral cavity to effectively clean teeth and to recycle that solution for its reuse by an individual. In accordance with an embodiment of the invention, the apparatus includes a tube and a pump disposed within a hand-holdable housing. The pump impels solution, which may contain abrasive particles or other cleaning media through a tube lumen and out of an exit nozzle defined at a distal end of the tube. The exit nozzle is located proximate to a distal opening defined by the housing. The solution is directed toward a vicinity of a surface in order to clean the surface. The pump also urges the solution back from the vicinity of the tooth surface through the distal opening. The apparatus provides for the reuse of the same solution and for cleaning a number of teeth by including a solution return path outside of the lumen. A preferred embodiment provides for a reservoir for storing solution and for receiving recycled solution. This reservoir may be disposed within the hand-held housing providing the capability of a self-contained, portable apparatus.

The apparatus may further include an orifice boot coupled to the housing proximate the distal opening. The apparatus may be made from material capable of being sterilized by ultraviolet or microwave radiation. Further, it may include a sensor to actuate the pump when a surface is contacted.

Pumping may be provided in accordance with the invention by a variety of mechanical methods including piston-based designs or non-mechanical methods, without limitation. An embodiment uses a pump based upon a stepped piston. Such a pump may be capable of synchronously pumping a first volume of fluid and a second volume of air.

Another embodiment of the invention uses a pump based upon a plurality of valves which may be actuated depending upon the position of a flexible membrane. The position of the membrane may be controlled by a second pressurized fluid.

In yet another embodiment, an apparatus for cleaning a surface with a cleaning solution includes a first pump for impelling solution, a second pump for urging solution which has been impelled, and a reservoir. A single pump may both impel solution toward and urge solution away from the vicinity of the surface.

In accordance with an embodiment of the invention, a method of cleaning a surface in an oral cavity comprises filling a reservoir with foaming-resistant solution, actuating a first pump to impel solution through a nozzle to the vicinity of the surface and holding the nozzle so that a second pump urges solution back through a solution return path so that solution may be recycled. A reservoir may be provided for holding solution.

Another embodiment provides a method of cleaning a tooth comprising holding a graspable housing, having a reservoir, tube, and pump disposed therein, such that an opening defined by the housing and an exit nozzle defined by the tube are in a vicinity of the tooth surface, actuating a pump to impel solution to and to urge solution from the vicinity of the tooth surface. The urged solution is returned to the reservoir via a return path from the opening in the housing and is capable of being recycled.

In yet another embodiment, a method for periodically cleaning a plurality of surfaces in an oral cavity is provided. The steps include grasping an apparatus previously described, actuating the pump, holding the distal opening so that the pump urges solution from the oral cavity to be recycled, repositioning the exit nozzle in the vicinity of another surface, and repeating the preceding steps. The method may further include storing the apparatus in a sterilizer and repeating all of the steps as required.

DESCRIPTION OF SPECIFIC EMBODIMENTS

Figure 1A:
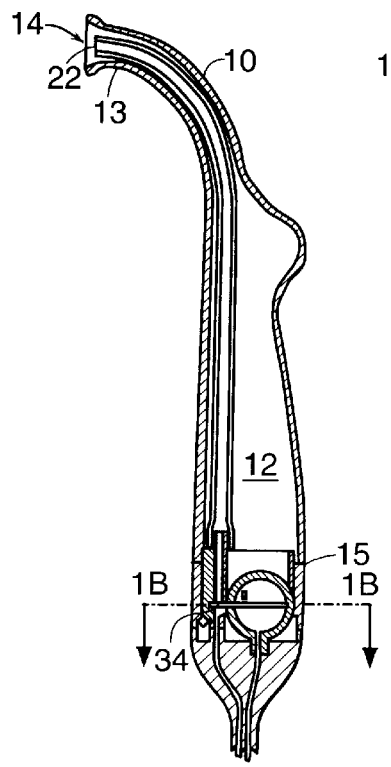
FIG. 1A is a longitudinal sectional view of an assembled apparatus according to an embodiment of the invention utilizing a membrane-based pump.
Figure 1C:
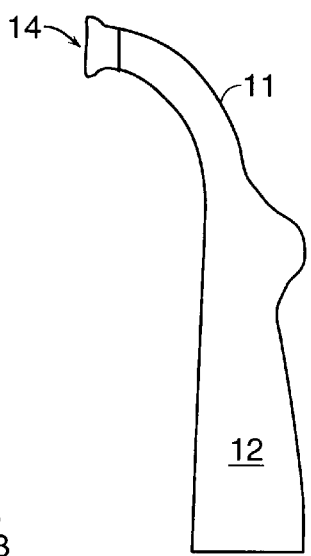
FIGS. 1C, 1D, and 1E depict elements of the apparatus according to the embodiment.
Figure 1E:
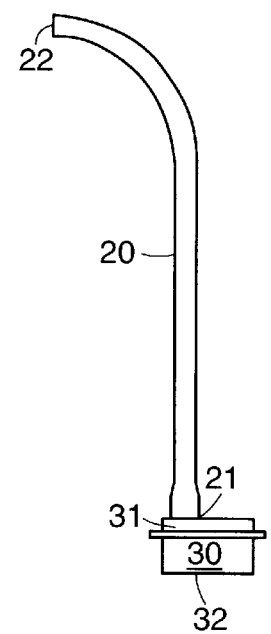

An embodiment of an apparatus to clean teeth includes a hand-holdable housing 10, a tube 20, and a pump 30, as shown in FIGS. 1A–E. FIG. 1E illustrates a proximal end 21 of the tube 20 coupled to a pump port 31. The pump 30 displays sufficient capacity, in accordance with the various embodiments described below, to both impel solution out of distal opening 14 and urge (or draw) solution back into distal opening 14 so as to recycle the cleaning solution. A membrane-based pump 30, having a first flexible membrane 32, is shown in FIGS. 1A, 1B, 1E and FIGS. 2–6. Such a pump 30 is actuated depending upon the position of membrane 32. The present invention is, in no way, limited to this type of pump. Apparatuses based upon a piston-based pump are shown, in accordance with other embodiments, in FIGS. 8–13.

Figure 1B:
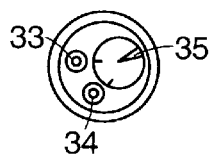
FIG. 1B shows a cross-sectional view of the pump interface which couples the reservoir with the tube in accordance with the embodiment.
Figure 1D:
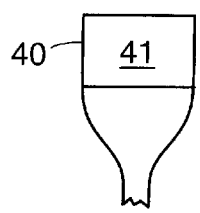

Regarding the embodiment of FIGS. 1A–E, solution is impelled by the pump 30, through the pump port 31, into the tube 20, exiting at a distal end of the tube, the distal end forming an exit nozzle 22. FIG. 1D shows a base 40. The base 40 is coupled with the pump 30 and operates, in accordance with the embodiment and further described below, to control the position of the first flexible membrane 32. FIG. 1C shows a housing shell 11 defining a reservoir 12 and shaped, in accordance with the embodiment, to facilitate comfortable, hand-held use. The shell 11 is coupled with an upper base portion 41, the pump encased within the upper base portion 41. The shell 11 defines a distal opening 14. An orifice boot 13, coupled to the shell 11 at its distal opening 14 may be provided, as shown. The shell 11, as well as the tube 20, should be made from materials designed to retain their shape during the intermittent or continuous application of pressure. The boot 13 may be made from rubber or other flexible material to provide comfort to the user. The boot 13 may have utility in facilitating the urging of solution from a vicinity of a dental surface (not shown), back through the distal opening 14, and returning to the reservoir 12 for reuse. Forward fluid communication is defined as maintaining a path for, for example, cleaning solution to flow from housing 10 to the vicinity of a surface to be cleaned. Return fluid communication is similarly defined as maintaining a path for cleaning solution to be urged from the vicinity and returned to housing 10. For embodiments which include a reservoir 12, forward fluid communication is that communication directed away from the reservoir 12 and return fluid communication is directed toward the reservoir 12.

FIG. 1B illustrates a cross-section of the pump 30, as viewed from above the housing 10, depicting an inlet valve 33, an exit valve 34, and a pumping chamber 35. The operation of the pump 30 is described, in detail, below. An assembled apparatus, as shown in FIG. 1A, shows the position of the exit nozzle 22 within the distal opening 14. FIG. 1A depicts a gasket 15 placed between the shell 11 and the upper base portion 41, substantially eliminating fluid leakage. FIG. 1B also shows the position of the exit valve 34 which, when open, allows pressurized solution to be impelled into the tube 20.

Figure 2:
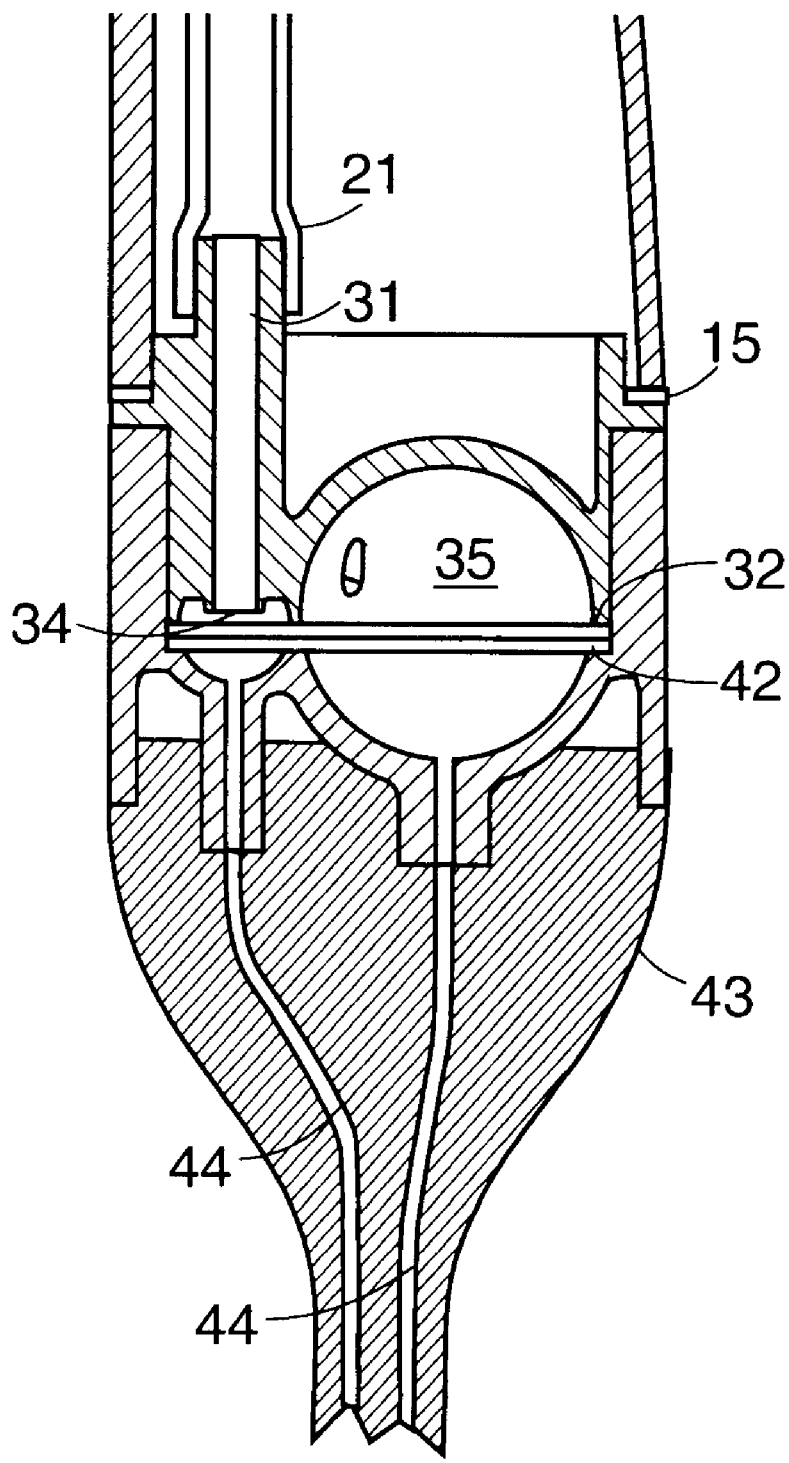
FIG. 2 is a sectional view of the membrane-based pump and base sections in accordance with an embodiment of the invention.

FIG. 2 is an enlargement of FIG. 1A and depicts the orientation of the exit valve 34, the pumping chamber 35, and the gasket 15, in an assembled apparatus. A second flexible membrane 42 is shown in contact with the first flexible membrane 32. The second flexible membrane 42 forms a boundary between the upper base portion 41 and a base control unit 43. The base control unit 43 may utilize a control fluid or other pressure transfer medium to exert force on the second flexible membrane 42, in turn exerting force on the first flexible membrane 32. In accordance with the depicted embodiment, channels 44 defined by the base control unit provide fluid communication between a control fluid source (not shown) and the second flexible membrane 42 in order to actuate the pumping and valving mechanisms. The control fluid may either remained sealed within the base control unit 43 or, alternatively, be provided from an external source (not shown).

Figure 3A:
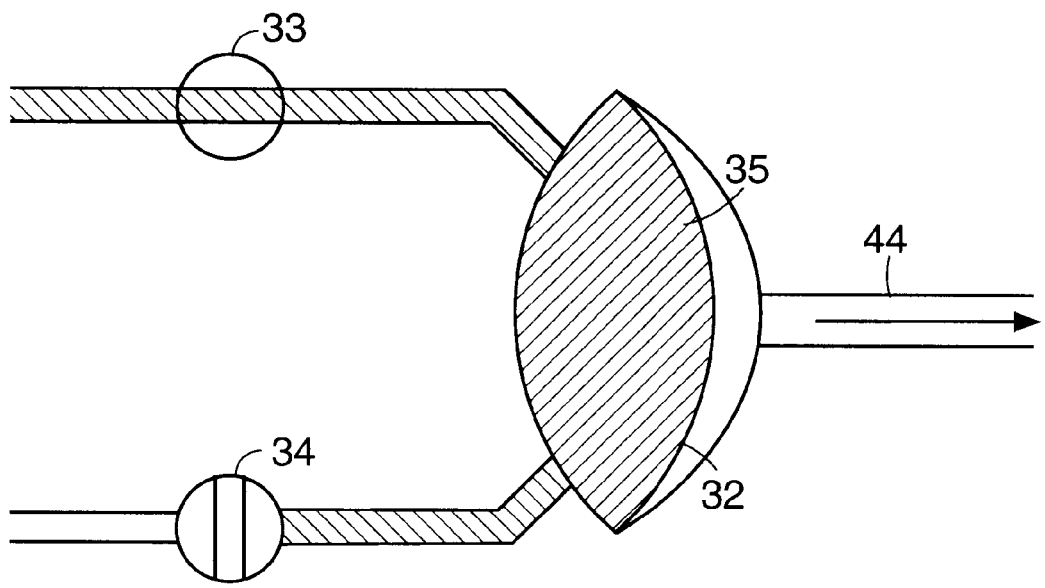
FIGS. 3A and 3B are schematic representations of membrane-based pumping and fluid flow according to an embodiment of the invention.
Figure 3B:
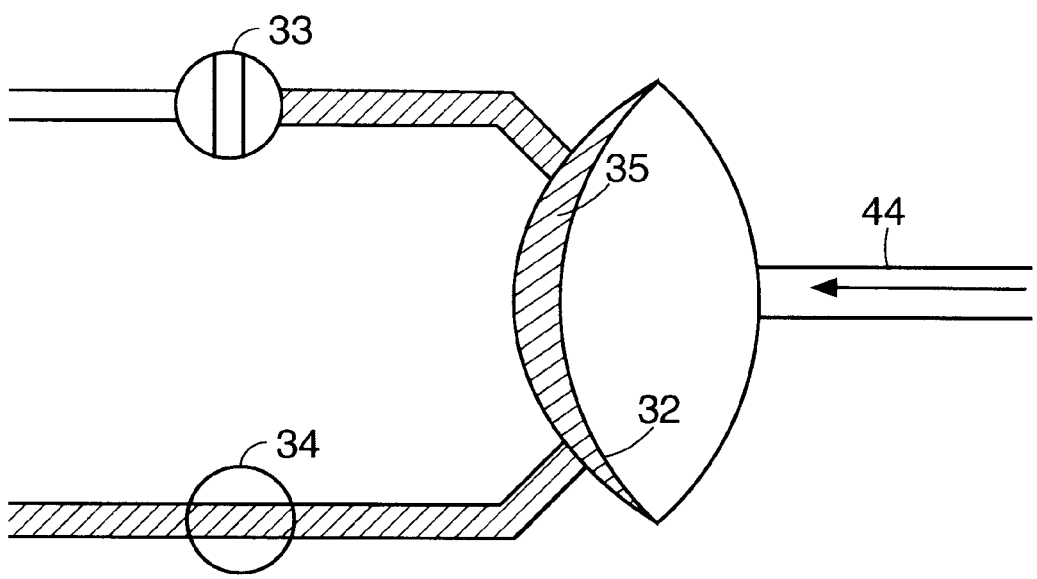

FIGS. 3A and B schematically illustrate a pumping sequence for a membrane-based pump 30 in accordance with an embodiment of the invention. FIG. 3A shows how the pumping chamber 35 fills with cleaning solution. When inlet valve 33 is open, flexible membrane 32 is forced to curve away from the inlet, allowing the pumping chamber 35 to fill. The control fluid is drawn away from the membrane 32 through a channel 44. The arrow shows the direction of control fluid flow. After the chamber 35 is substantially full, the second part of the sequence is initiated. Control fluid is forced back through channel 44 against the membrane 32, as shown in FIG. 3B, after the closing of inlet valve 33 and the opening of exit valve 34. Solution is impelled from the chamber 35 and the membrane 32 curves toward the inlet. The control fluid fills the chamber 35 and remains until the first part of the sequence is iterated.

Figure 4A:
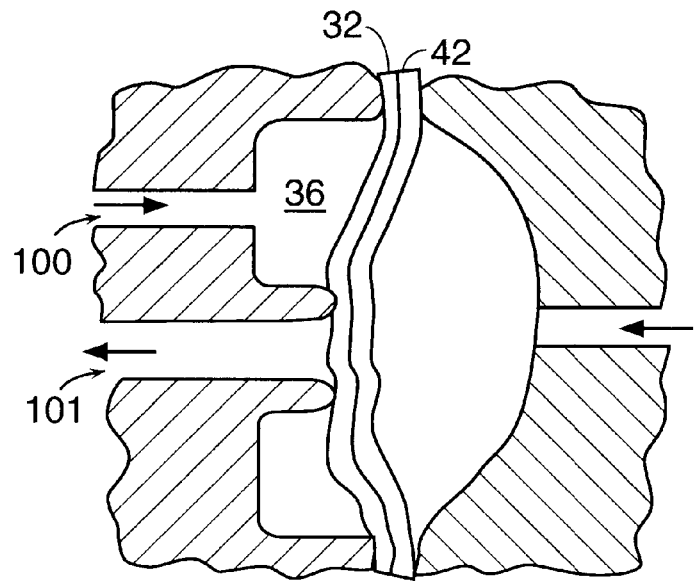
FIGS. 4A and 4B are representations of valve actuation in accordance with an embodiment of the invention.
Figure 4B:
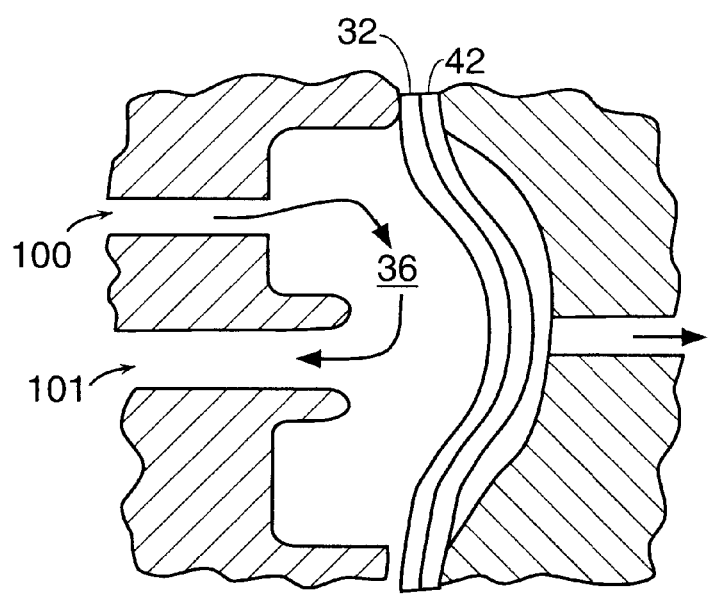
Figure 5A:
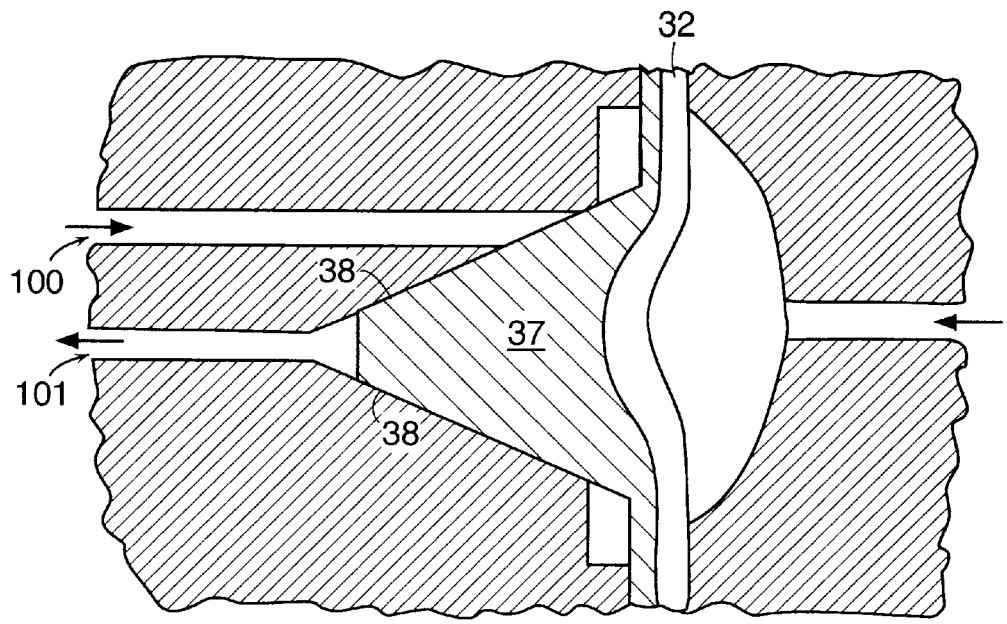
FIGS. 5A and 5B are representations of a valve design and its actuation in accordance with a specific embodiment of the invention.
Figure 5B:
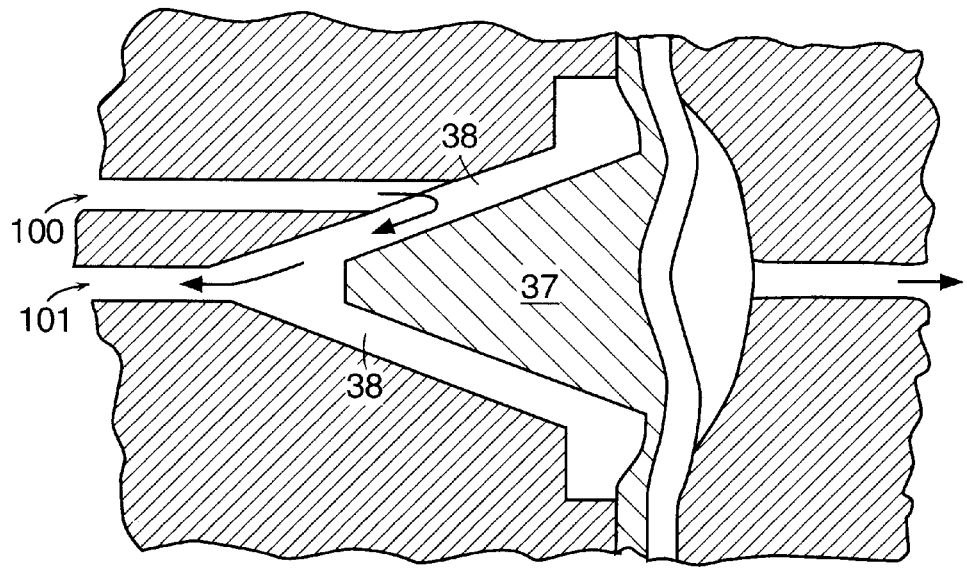
Figure 6A:
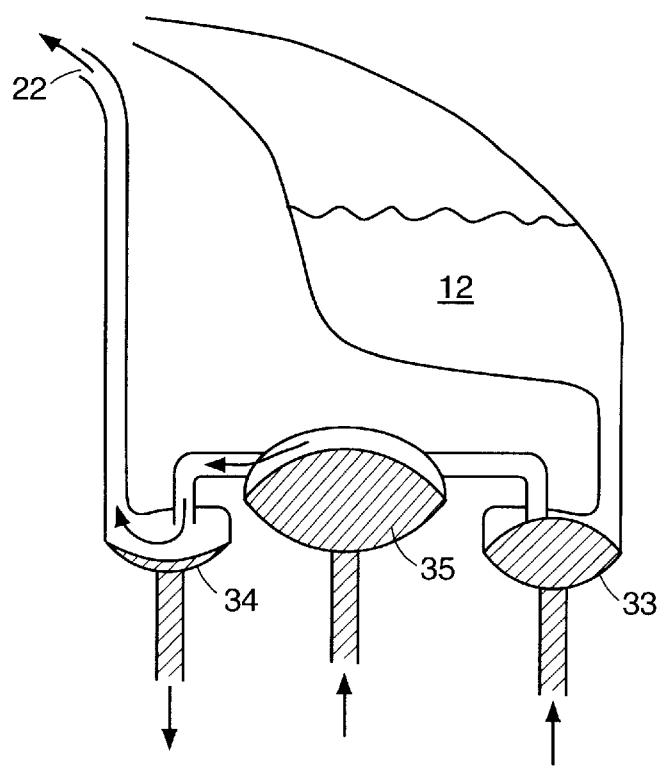
FIGS. 6A and 6B are schematic representations of fluid flow according to a specific embodiment.
Figure 6B:
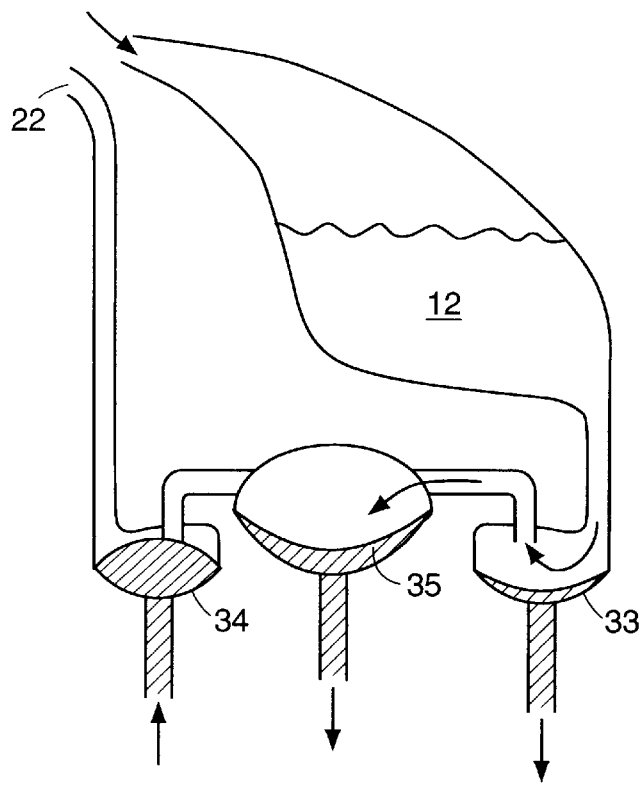

FIGS. 4A and 4B illustrates a design for an inlet or exit valve according to an embodiment of the invention. These valves may be of the type disclosed in U.S. Pat. No. 5,088,515 for an invention of Kamen. FIGS. 5A and 5B show an alternate valve design. Either of these designs, as well as others within the spirit of the invention, may be incorporated into the pump represented in FIGS. 6A and 6B. Fluid enters the valves of FIGS. 4A and 4B and FIGS. 5A and 5B at entry 100 and exits the valves at exit 101. FIGS. 6A and 6B illustrate the flow of solution from the reservoir 12, through a physically distinct inlet valve 33, pumping chamber 35, and exit valve 34. A representation of control fluid flow is, also, illustrated. In the embodiment of the valve design of FIGS. 4A and 4B, a second flexible membrane 42 is shown to be in contact with the first flexible membrane 32. In this design, solution allowed to enter entry 100 flows into a region 36 and is then forced out of region 36 into exit 101. In the embodiment of the valve design of FIGS. 5A and 5B, the membrane 32 is used to force a conical shaped valve part 37 toward and away from a mating cavity defined by the body of the pump 30. This design may provide superior valve seating and increased impelling and urging force.

Figure 7:
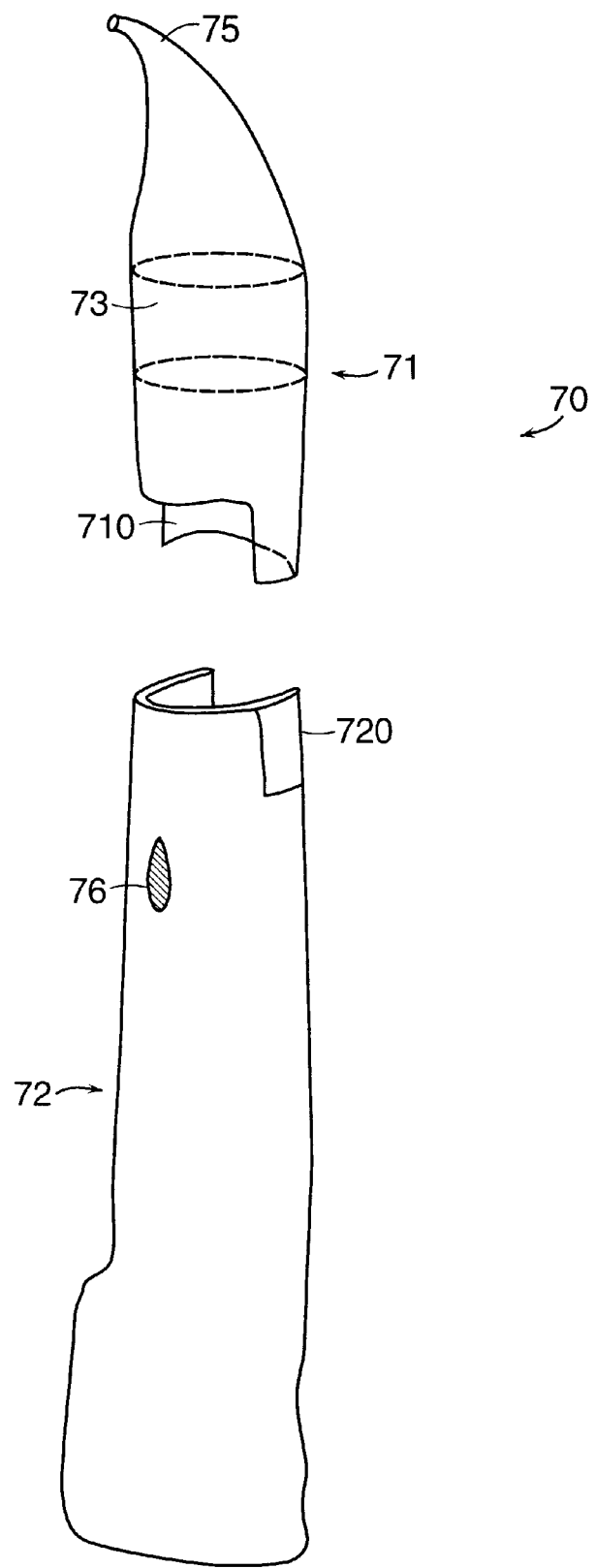
FIG. 7 is an exploded view of an apparatus in accordance with a further embodiment.

FIG. 7 is an exploded view of an apparatus for cleaning teeth in accordance with a further embodiment. Apparatus 70 is shown to have both a personal unit 71 and a base unit 72 which are easily attached or separated. Base unit 72 may be used by multiple users, while personal unit 71 is designed specifically for a single user to respect personal hygienic considerations. As will be further detailed below, solution, including a portion recycled from the user's oral cavity, flows only through personal unit 71. In this embodiment, a reservoir 73 (shown schematically as a volume between dashed line boundaries) is disposed within personal unit 71. FIG. 7 illustrates an embodiment for attaching personal unit 71 to base unit 72. A personal unit housing portion 710 is cut out and a matching base unit housing portion 720 is also cut out facilitating release of personal unit 71 from apparatus 70 by sideways or lateral motion of personal unit 71. Fixation of personal unit 71 to base unit 72 may be accomplished by fastening mechanisms known in the art. A core component (shown as item 87 in FIG. 8) is positioned inside unit 71. Core 87 may include protrusions or slots to further fix units 71 and 72 in place during operation of apparatus 70. Switch 76 is conveniently disposed on base unit 72 so that a user may conveniently turn apparatus 70 on and off. A power source (not shown) may conveniently be stored in the base unit 72 in power communication with switch 76. In addition, a sensor 77 (not shown in FIG. 8) may be strategically placed to automatically effectuate activation of apparatus 70. By way of examples, a pressure sensor in the exit nozzle 75 may be included in order to activate apparatus 70 in the case when the exit nozzle 75 contacts a surface. A photo sensor might be used to activate the apparatus 70 when the exit nozzle 75 is placed into the mouth of a user causing in a reduction in sensed light.

Figure 8:
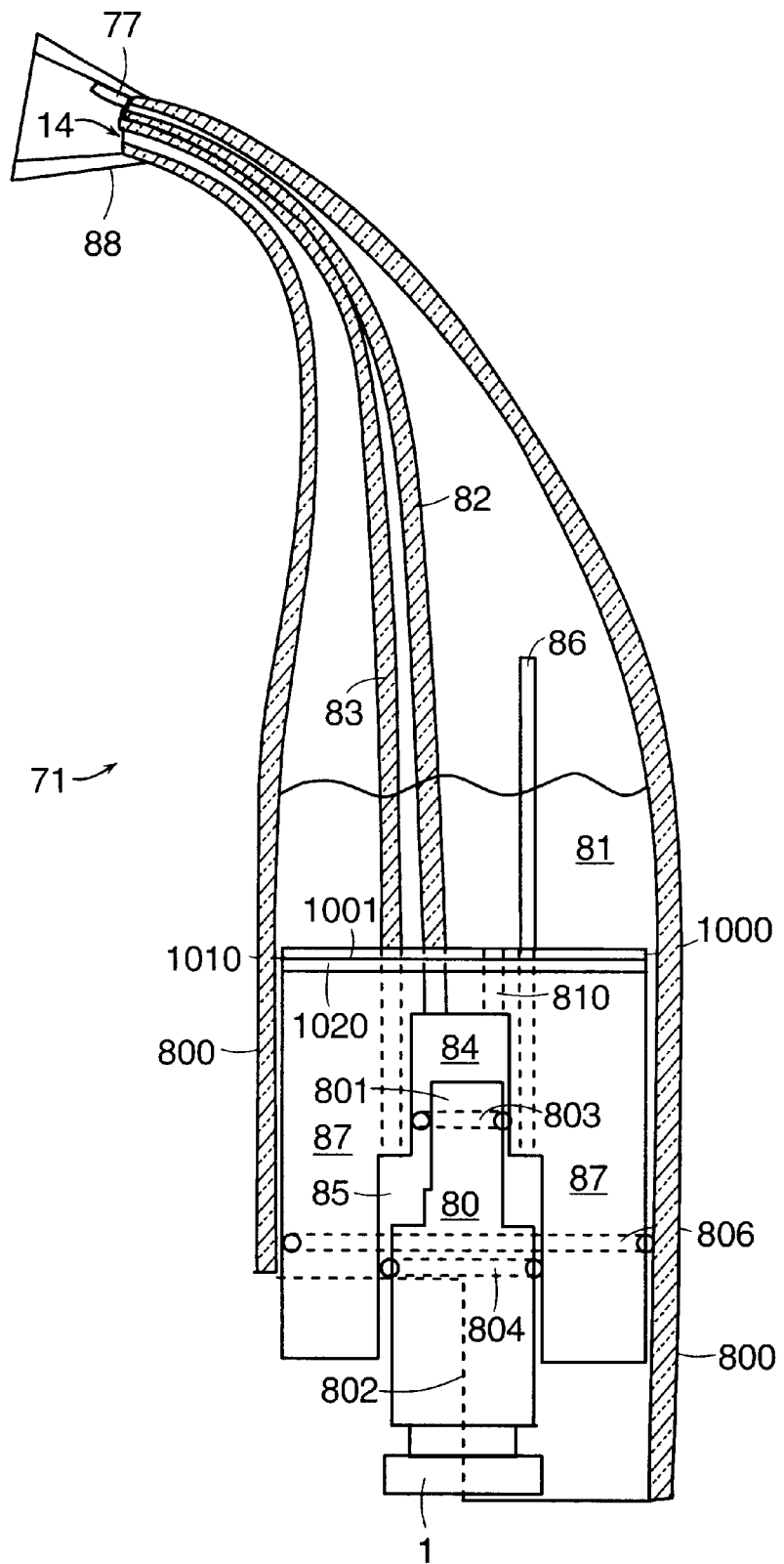
FIG. 8 is a cross-sectional view of a personal unit according to another embodiment.

FIG. 8 is a cross-sectional view of a personal unit 71 in accordance with an embodiment which uses a piston-based pump. A pump using a stepped piston head 80 provides the power necessary to impel solution from reservoir 81, through solution outlet line 82 and out of personal unit 71 through distal opening 14. In addition, the pump urges solution back through opening 14, and pumps air out through air outlet line 83, and, because of the partial vacuum created in second pump chamber 85, urges air back into second pump chamber 85 via air inlet 86. Solution is in fluid communication between reservoir 81 and first pump chamber 84 via line 810 controlled by a flapper valve detailed below or by other valving arrangements, including, but not limited to, duckbill and umbrella valves known in the art. Pump chambers 84 and 85 are disposed within core 87 which is sized to fit within housing 800. The term "ganged pump" is used to describe this type of pump designed to perform a number of functions given the limited size of housing 800 in a dimension perpendicular to the pumping direction. Embodiments of a ganged pump are disclosed in a concurrently filed U.S. Provisional Application, Serial No. 60/126,518, entitled "Ganged Pump Driven by a Single Piston", the Application listing as inventor Larry B. Gray, the Application hereby incorporated herein by reference. An upper head portion 801 mated with first pump chamber 84 is ganged, along the pumping direction, with a lower head portion 802 mated with second pump chamber 85 so that, unlike a reciprocating pump (for which one chamber may pump while another fills), motion of head 80 into core 87 results in the pumping of both first pump chamber 84 and second pump chamber 85 resulting in the timed expulsion of both solution, from first pump chamber 84, and air, from second pump chamber 85. Motion of head 80 into core 87 facilitates (described below) both the filling of first pump chamber 84 with solution retrieved from reservoir 81 and the urging of air from housing 800 into second pump chamber 85. O-rings 803 and 804 prevent fluid communication between chambers 84 and 85. Core O-ring 806 provides a seal between housing 800 and core 87 preventing unintended fluid communication between reservoir 81 and other components of apparatus 70. An orifice boot 88 is shown fitting around distal opening 14. The boot 88 may assist operation of apparatus 70 in a number of ways. First, if made of rubber or a compliant polymer, boot 88 provides a palatable cushion for a user to comfortably place in the mouth. It may also provide a degree of sealing with a tooth surface toward which the apparatus 70 is directed as well as provide added directionality for the solution and air flow. Further, it may afford assistance in urging solution back into apparatus 70. Additionally, a mechanical wiping of surfaces may be accomplished as orifice boot 88 is moved to different surfaces and locations in the mouth resulting in additional cleaning benefit. Orifice boot 88 may readily be detached from distal opening 14 and is replaceable.

Figure 9:
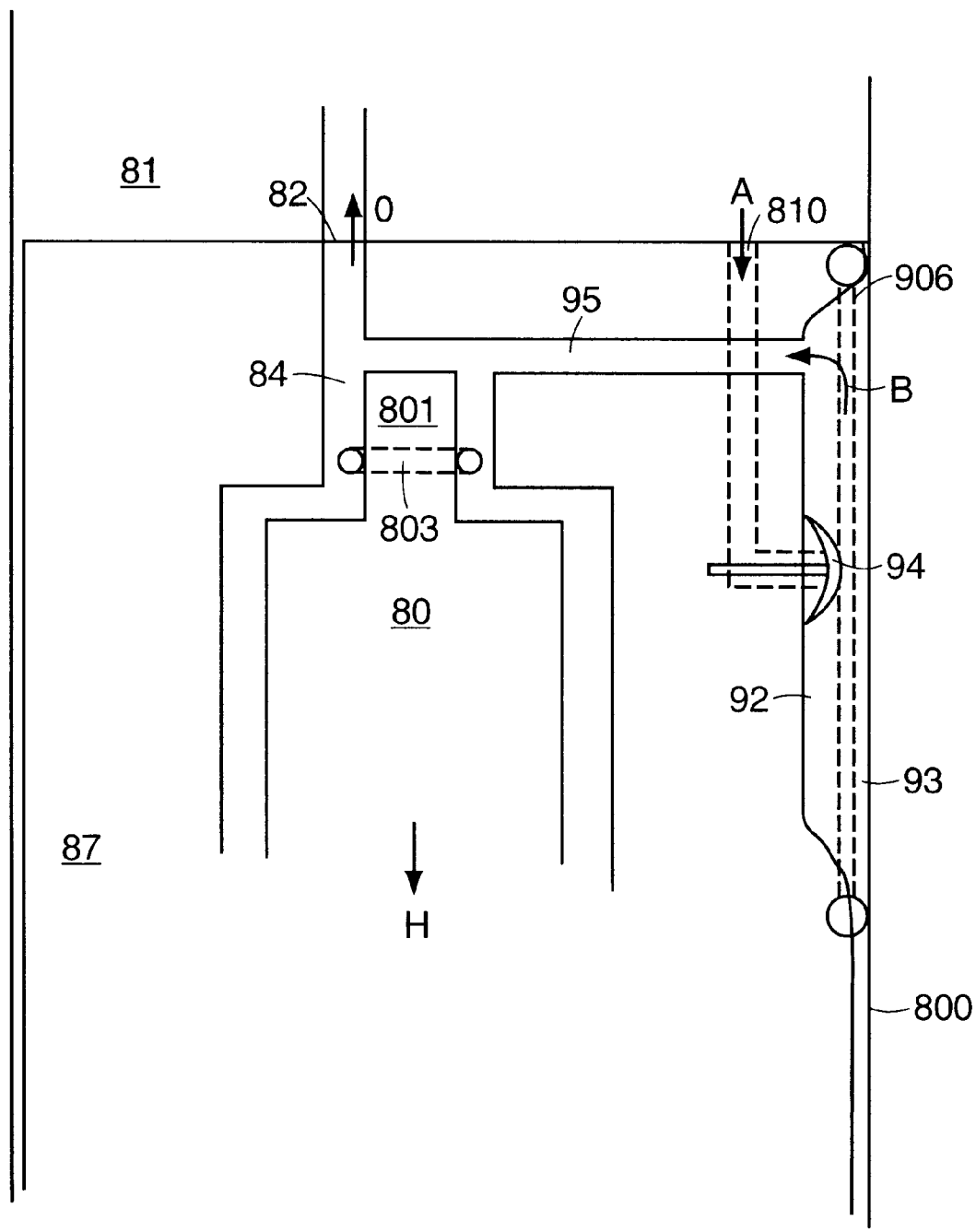
FIG. 9 is a cross-sectional view of a core according to an embodiment of the invention.

FIG. 9 is a cross-sectional view of a core 87 illustrating, in accordance with an embodiment of the invention, a mechanism for establishing forward fluid communication between the reservoir 81 and solution outlet line 82. A reservoir outlet passage 810 is disposed in core 87. A cut-out core portion 92, creates, when core 87 is operational within housing 800, an umbrella valve chamber 93 within housing 800. Motion of head 80 out of core 87 (direction H) facilitates filling of first pump chamber 84 with solution retrieved from reservoir 81. Solution first flows from reservoir 81 via reservoir outlet line 810 in direction A. The motion of head 80 causes a partial vacuum to be created in first pump chamber 84. This causes umbrella valve 94 to open as the pressure difference is conveyed from first pump chamber 84 via solution inlet passage 95 disposed in core 87 and umbrella valve chamber 93. Solution fills first pump chamber 84 via solution inlet passage 95 in direction B until head 80 begins moving into core 87 (opposite direction from direction H). Relief of the partial vacuum in this part of the head 80 cycle of movement causes umbrella valve 94 to close and remain closed until upper head portion 801 begins to, again, move out of core 87 (direction H). Solution is impelled through solution outlet line 82 in direction O and first pump chamber 84 again becomes empty. Umbrella valve 94 is preferably made from a flexible material so that it deforms when pressure in reservoir 81 is higher than the pressure in umbrella valve chamber 93 but will be held against core 87 when the pressure in umbrella valve chamber 93 is higher than the pressure in reservoir 81. Umbrella chamber O-ring 906 is provided to seal umbrella valve chamber 93 and solution contained within from the rest of apparatus 70.

Figure 10:
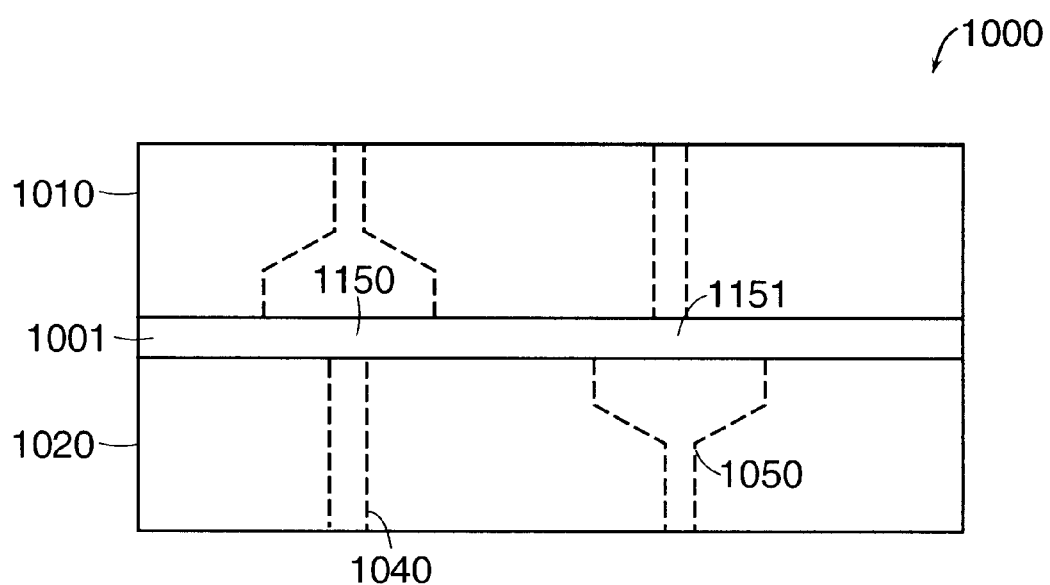
FIG. 10 is a cross-sectional representation of a tri-layer valve assembly.
Figure 11A:
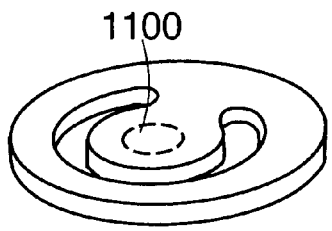
FIG. 11A is a perspective view of a membrane valve.
Figure 11B:
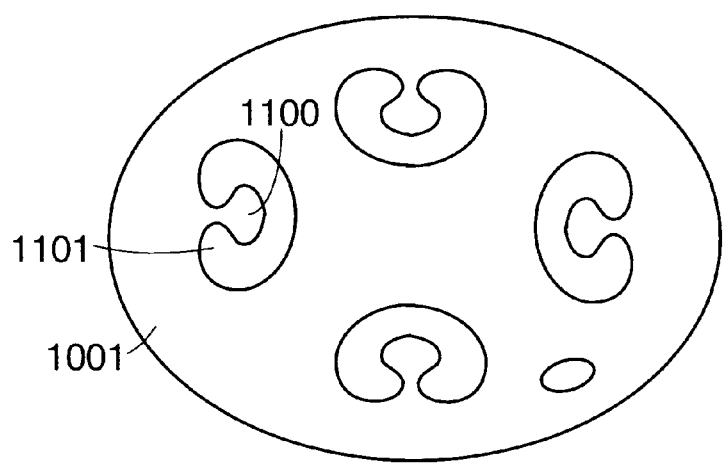
FIG. 11B is a top view of a membrane sheet.
Figure 11C:
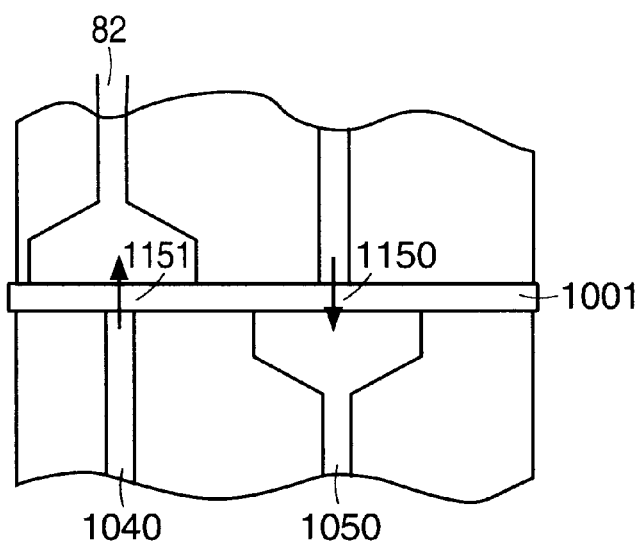
FIG. 11C is a cross-sectional representation showing fluid communication afforded by a tri-layer valve assembly.

FIGS. 10 and 11A–C illustrate, in more detail, the valve assembly 1000 of FIG. 8. FIGS. 10 and 11C are cross-sectional views of a pair of the four valves of tri-layer valve assembly 1000 formed and positioned at the surface of the core 87 which forms the floor of reservoir 81. The position of assembly 1000 is depicted in FIG. 8. Assembly 1000 has a flexible membrane 1001 sandwiched between an upper assembly portion 1010 and a lower assembly portion 1020. This assembly 1000 creates four flapper valves (FIG. 11B); such valves are known in the art. The valves are one-way valves. Two flapper valves are provided for each of the solution flow path (one valve controlling the path from reservoir 81 to first pump chamber 84; a second controlling the path from first pump chamber 84 to solution outlet line 82) and the air flow path (one valve controlling the path from air inlet 86 to second pump chamber 85; a second controlling the path from second pump chamber 85 to air outlet line 83). Membrane 1001 is shaped so that each flapper valve 1100 is defined by a slot 1101 partially surrounding valve 1100. Membrane 1001 is flexible so that valve 1100 can be moved out of the plane of membrane 1001. Inlet channel 1040 has a smaller diameter than the dimension of slot 1101; outlet channel 1050 has a larger diameter than slot 1101. So, as previously discussed, motion of head 80 out of core 87 causes a partial vacuum to be created in second pump chamber 85. When pressure in outlet channel 1050 below membrane 1001 is less than pressure above membrane 1001, valve 1150 (FIG. 11C) will open sending air into chamber 85. Conversely, valve 1151 will be closed and air will not flow to air outlet line 83 until pressure in inlet channel 1040 is higher below membrane 1001 than above membrane 1001. This occurs when air has filled chamber 85 and piston head 80 begins to move into core 87. Valve 1151 then opens and air is pumped out of chamber 85 into line 83. Analogous response of the solution line valves occurs. Preferredly, assembly 1000 will have standard registration pins or detents so that its inlet and outlet flow channels may be aligned with the appropriate passages provided in core 87. Assembly 1000 should be removable to facilitate cleaning.

Figure 12A:
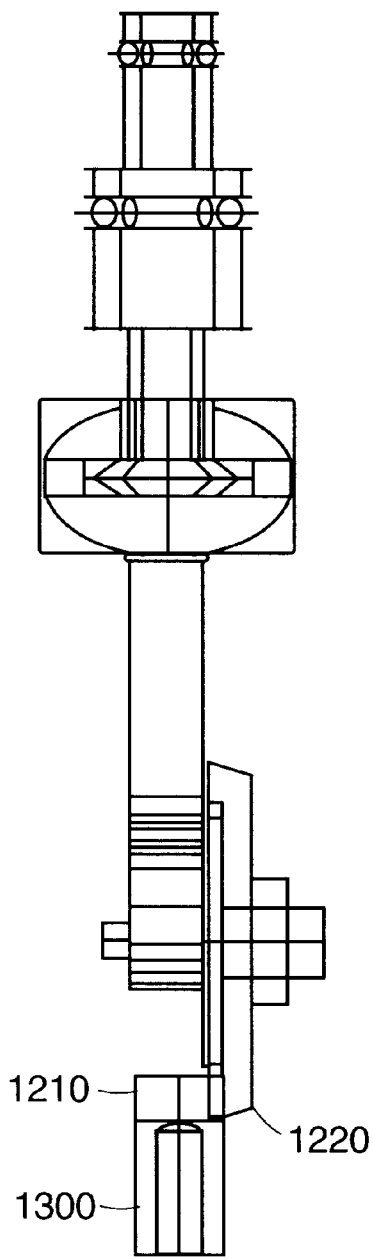
FIGS. 12A–B are longitudinal views of a Scotch yoke used to convert rotary to linear motion.
Figure 12B:
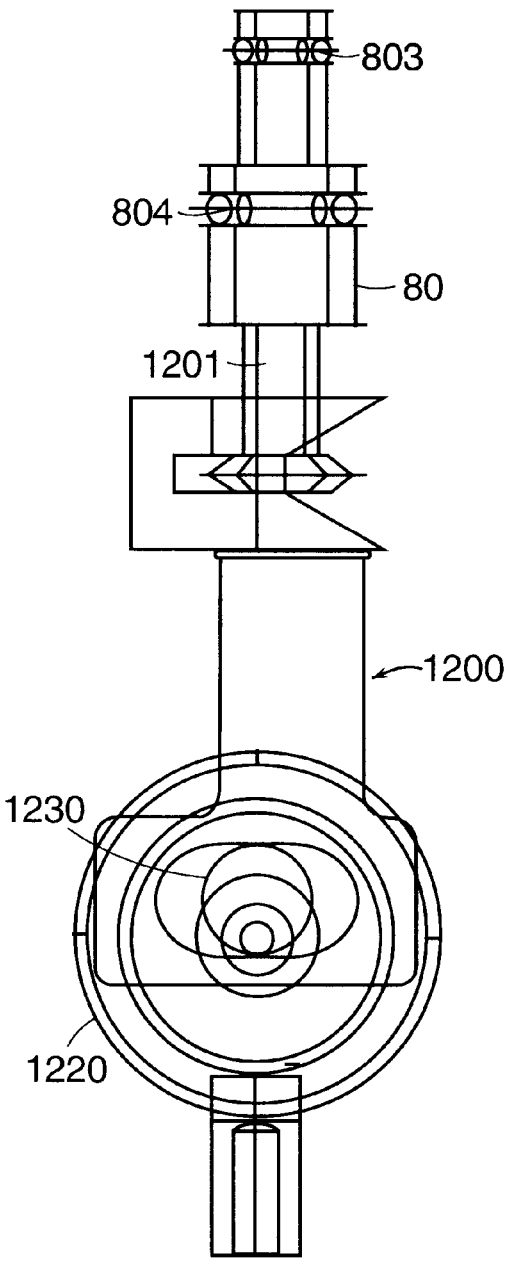

FIGS. 12A–B are front and side longitudinal views of a Scotch yoke 1200. Scotch yokes 1200 shown coupled with head 80 by a piston rod 1201 and coupled to motor shaft 1300 by first gear 1210, second gear 1220, and offset cam 1230 are known in the art as effective devices for converting the rotary motion of a motor shaft 1300 to an up and down motion of a head 80.

Figure 13:
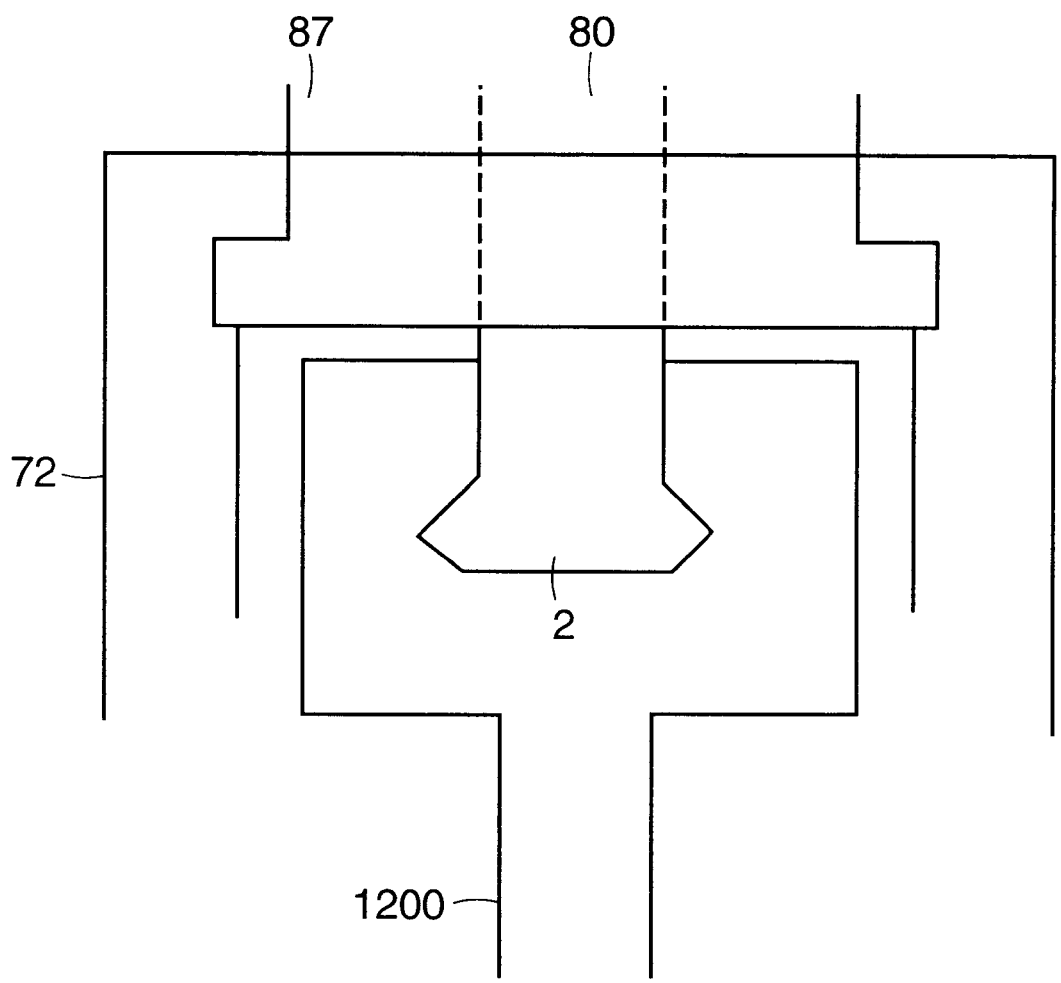
FIG. 13 is a cross-sectional view of an alternate piston head shape and how it may be coupled with a Scotch yoke.

FIG. 13 illustrates, in cross-sectional view, an alternate, preferred shape for an opposite end of stepped piston head 80 and how head 80 is coupled with Scotch yoke 1200. The alternate shape 2 (opposed to shape 1 of FIG. 8) is preferred for practical assembly considerations.

Methods of cleaning a surface in an oral cavity by actuating a pump 30, such as those described above, both to impel solution to a vicinity of a tooth surface and holding an exit nozzle 22 to urge the recycling of that solution provide additional embodiments of the present invention. Another embodiment of the invention further includes the use of a hand-holdable housing which may have a reservoir for holding a volume of fluid disposed within. An embodiment for a system for periodically cleaning a plurality of surfaces is an additional aspect of the present invention.

Although the invention has been described with reference to several preferred embodiments, it will be understood by one of ordinary skill in the art that various modifications can be made without departing from the spirit and the scope of the invention, as set forth in the claims hereinbelow.

We claim:

1. An apparatus for cleaning a surface within a mouth of a person, the apparatus capable of recycling a cleaning solution, the apparatus comprising:
    a hand-holdable housing having a distal opening;
    a tube disposed substantially within the housing, the tube having a lumen, a proximal end, and a distal end defining an exit nozzle, the exit nozzle located proximate to the distal opening;
    a pump disposed within the housing for both impelling the solution through the lumen of the tube causing the solution to exit the lumen through the exit nozzle and be directed into the mouth of the person to a vicinity of the surface and for drawing the solution from the vicinity of the surface in the mouth of the person; and
    a solution return path providing fluid communication outside the lumen between the vicinity and the proximal end for recycling the drawn solution.

2. An apparatus according to claim 1, further comprising:
    an orifice boot coupled to the housing proximate the distal opening.

3. An apparatus according to claim 1, wherein the housing, the tube, and the pump are made from material transparent to and are capable of being sterilized by ultraviolet radiation.

4. An apparatus according to claim 1, further comprising:
    a sensor;
    the sensor capable of actuating the pump when the apparatus contacts the surface.

5. An apparatus according to claim 1, the surface being within an oral cavity of a user, the user having a mouth, the apparatus further comprising:
    a sensor;
    the sensor capable of actuating the pump when the mouth is closed and the exit nozzle is within the oral cavity.

6. An apparatus according to claim 5, wherein the sensor is also capable of actuating the pump when the apparatus contacts the surface.

7. An apparatus as in claim 1, further comprising:
    a reservoir, disposed in the solution return path, for containing a volume of solution.

8. An apparatus according to claim 7, wherein the volume includes solution both before it is impelled by the pump and solution after it is urged by the pump so that urged solution is capable of being impelled.

9. An apparatus according to claim 7, wherein the housing, the tube, the pump, and the reservoir are made from material transparent to ultraviolet radiation.

10. An apparatus according to claim 7, wherein the housing, the tube, the pump, and the reservoir are made from material suitable for sterilization by exposure to microwave radiation.

11. An apparatus according to claim 7, wherein the reservoir is disposed within the housing.

12. An apparatus according to claim 1, wherein the pump includes a piston.

13. An apparatus according to claim 7, wherein the pump includes a piston.

14. An apparatus according to claim 1, wherein the pump includes a ganged pump.

15. An apparatus according to claim 14, wherein the pump synchronously pumps a first volume of the cleaning solution and a second volume of air in such a manner as to create a vacuum for drawing the solution from the mouth of the person into the apparatus.

16. An apparatus according to claim 1, wherein the pump includes a flexible membrane for impelling the cleaning solution through the lumen of the tube.

17. An apparatus according to claim 16, wherein a pressurized fluid is used to control a position of the flexible membrane.

18. An apparatus for cleaning a surface with a cleaning solution, the apparatus comprising:
    a reservoir for containing a volume of the cleaning solution;
    a first pump chamber for impelling, upon motion of a piston, the cleaning solution toward a vicinity of the surface; and
    a second pump chamber for urging, upon motion of the piston, the cleaning solution from the vicinity of the surface for recycling into the reservoir;
    the pump chambers disposed within a hand-holdable housing and the volume including solution both before it is impelled by the first pump chamber and solution after it is urged by the second pump chamber so that urged solution is capable of being impelled.

19. A method of cleaning a surface in an oral cavity comprising the steps of:
    filling a reservoir with cleaning solution,
    impelling the solution from the reservoir and out of an exit nozzle toward a vicinity of the surface, and
    holding the exit nozzle in a position such that a pump urges solution from the vicinity of the surface back to the reservoir.

20. A method according to claim 19, wherein the solution is contained in a reservoir both before it is impelled and after it is urged, so that urged solution is capable of being impelled.

21. A method of cleaning a surface in an oral cavity comprising the steps of:
    grasping a hand-holdable housing, the housing having a reservoir, a tube and a pump disposed therein, the tube having a lumen and a distal end defining an exit nozzle, the housing having a distal opening such that the exit nozzle is located proximate to the distal opening, wherein the reservoir, the pump, and the tube are in forward fluid communication, the housing defining a solution return path affording return fluid communication between the distal opening and the reservoir, such that the exit nozzle is in a vicinity of the surface, actuating the pump to impel a foaming-resistant solution contained in the reservoir out of the exit nozzle, the solution directed toward the vicinity of the surface, and holding the distal opening in the vicinity of the surface so that the pump urges solution from the vicinity of the surface, recycling the solution back into the reservoir through the solution return path.

22. A method according to claim 21, wherein, in the step of actuating, actuating is performed using a sensor.

23. A method for periodically cleaning a plurality of surfaces in an oral cavity comprising the steps of:

grasping a hand-holdable housing, the housing having a reservoir, a tube and a pump disposed therein, the tube having a lumen and a distal end defining an exit nozzle, the housing having a distal opening such that the exit nozzle is located proximate to the distal opening, wherein the reservoir, the pump, and the tube are in forward fluid communication, the housing defining a solution return path affording return fluid communication between the distal opening and the reservoir, such that the exit nozzle is in a vicinity of a surface, actuating the pump to impel a solution contained in the reservoir out of the exit nozzle, the solution directed toward the vicinity of the surface, holding the distal opening in the vicinity of the surface so that the pump urges solution from the vicinity of the surface, recycling the solution back into the reservoir through the solution return path, repositioning the exit nozzle such that the exit nozzle is in a vicinity of another surface within the oral cavity, and repeating the step of repositioning as desired.

24. A method according to claim 23, further comprising the steps of:

storing the housing, reservoir, tube, and pump in a sterilizer in which exposure to radiation can occur, and periodically repeating the preceding steps.

25. A method according to claim 23, further comprising the step of:

providing a foaming-resistant solution for placement in the reservoir.

26. A method according to claim 23, wherein in the step of grasping, an orifice boot is coupled to the housing proximate the distal opening.

* * * * *

UNITED STATES PATENT AND TRADEMARK OFFICE
CERTIFICATE OF CORRECTION

PATENT NO. : 6,155,824
DATED : December 5, 2000
INVENTOR(S) : Kamen et al

It is certified that error appears in the above-identified patent and that said Letters Patent is hereby corrected as shown below:

In the name of the assignee, change "Partners" to --Partnership--

Signed and Sealed this

Twenty-ninth Day of May, 2001

Attest:

NICHOLAS P. GODICI

Attesting Officer      Acting Director of the United States Patent and Trademark Office